(12) United States Patent
Sakurai et al.

(10) Patent No.: US 8,494,873 B2
(45) Date of Patent: Jul. 23, 2013

(54) ENDOSCOPIC INSPECTION INFORMATION ADMINISTERING SYSTEM, ENDOSCOPIC INSPECTION INFORMATION ADMINISTERING METHOD AND COMPUTER READABLE MEDIUM

(75) Inventors: Hidehito Sakurai, Tokyo (JP); Takayoshi Kiuchi, Tokyo (JP); Ryojiro Sasage, Kanagawa (JP); Koichiro Miyazaki, Tokyo (JP); Yoshifumi Fukuyama, Tokyo (JP); Yasuhiro Asai, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 142 days.

(21) Appl. No.: 12/894,276

(22) Filed: Sep. 30, 2010

(65) Prior Publication Data
US 2011/0077961 A1 Mar. 31, 2011

(30) Foreign Application Priority Data
Sep. 30, 2009 (JP) ................................ 2009-228668

(51) Int. Cl.
*G06Q 40/00* (2012.01)
(52) U.S. Cl.
USPC .................................................. 705/2; 705/3

(58) Field of Classification Search
USPC .............................................................. 705/2
See application file for complete search history.

(56) References Cited

U.S. PATENT DOCUMENTS

2002/0026478 A1* 2/2002 Rodgers et al. ............... 709/205
2008/0243878 A1* 10/2008 de Spiegeleer et al. ....... 707/100
2009/0248441 A1* 10/2009 Okada .............................. 705/2

FOREIGN PATENT DOCUMENTS
JP 2004-348687 A 12/2004

* cited by examiner

*Primary Examiner* — Valerie Lubin
*Assistant Examiner* — Reginald R Reyes
(74) *Attorney, Agent, or Firm* — Sughrue Mion, PLLC (57) ABSTRACT

An endoscopic inspection information administering system includes: an unlinking unit for canceling a link between a first piece of inspection request information selected from the inspection request information on a database and a first piece of inspection result information linked with the first piece of the inspection request information; a retrieval display unit for retrieving, from the database, second pieces of the inspection request information including the same patient ID as a patient ID included in the first piece of the inspection request information and displaying the retrieved second pieces of the inspection request information, and a recording control unit for recording, into the database, a piece of the inspection request information selected from the displayed second pieces of the inspection request information in link with the first piece of the inspection result information.

8 Claims, 5 Drawing Sheets

| FUJISUKE FUJI ♂AB (+) 01234 31 YEARS OLD (1977.11.11) INPATIENT BUILDING ABC (301) | RESERVATION DETAILS | RETRIEVED ORDER LIST | INTERVIEW/ PRE-TREATMENT | INSPECTION RECORD | IMAGE CAPTURE/ REGISTER | IMAGE DISPLAY | REPORT | PATHOLOGY | CONDUCT | OPTION |

| ACCEPT | CANCEL | REGISTER RESERVATION | EDIT RESERVATION | DELETE | LINK | UNLINK | | PRINT ON ACCEPTANCE | PRINT LIST | OUTPUT FILE |

| VISIT | ACCEPT | INSPECT | BILL | PATIENT ID | NAME | BIRTH DATE | AGE | SEX | ORDER NUMBER | SCHEDULED DATE | SCHEDULED TIME | INPATIENT/ OUTPATIENT DISTINCTION | INSPECTION ITEM |
|---|---|---|---|---|---|---|---|---|---|---|---|---|---|
| ○ | ○ | ○ | ○ | 01234 | FUJISUKE FUJI | 1977/11/11 | 31 | MALE | 111111122222 | 2008/12/11 | 11:30 | INPATIENT | UPPER |
| ○ | ○ | ○ | ○ | 01235 | FUJIO FUJI | 1985/12/12 | 23 | MALE | 111111122222 | 2008/12/11 | 12:00 | OUTPATIENT | UPPER |
| ○ | ○ | | | 01235 | FUJIO FUJI | 1985/12/12 | 23 | MALE | 111111333322 | 2008/12/13 | 16:40 | OUTPATIENT | LOWER |
| | | | | 01237 | FUJIKO FUJI | 1985/12/12 | 23 | FEMALE | 111234561111 | 2008/12/12 | 09:30 | OUTPATIENT | UPPER |
| | | | | 01238 | MASAHARU FUJIYAMA | 1969/02/06 | 39 | MALE | 111112345611 | 2008/12/12 | 12:50 | INPATIENT | UPPER |
| | | | | 01239 | FUSHIMI FUJI | 1985/12/12 | 23 | FEMALE | 111111143215 | 2008/12/14 | 10:30 | INPATIENT | BRONCHIAL |

LOGIN NAME: AAA  LOGOUT

FIG. 5

|  | LIST OF CANDIDATES TO BE LINKED | | | DECIDE |
|---|---|---|---|---|
| INSPECTION RESULT INFORMATION | PATIENT ID | NAME | ......... | INSPECTION ITEM |
| PATIENT ID: 01235<br>INSPECTION ITEM: LOWER<br>INSPECTION DATE AND TIME:___/__/__ | 01235 | FUJIO FUJI | __/__/__ | UPPER |
| | 01235 | FUJIO FUJI | __/__/__ | LOWER |

ENDOSCOPIC INSPECTION INFORMATION ADMINISTERING SYSTEM, ENDOSCOPIC INSPECTION INFORMATION ADMINISTERING METHOD AND COMPUTER READABLE MEDIUM

CROSS-REFERENCE TO RELATED APPLICATIONS

This application is based on and claims priority under 35 USC 119 from Japanese Patent Application No. 2009-228668 filed on Sep. 30, 2009; the entire contents of which are incorporated herein by reference.

BACKGROUND

1. Technical Field

The present invention relates to an endoscopic inspection information administering system, an endoscopic inspection information administrating method and a computer readable medium in which inspection request information and inspection result information of endoscopic inspection are recorded in link with each other so that the information about the inspection can be managed.

2. Related Art

Since a plurality of inspection items such as upper, lower and bronchial are included in endoscopic inspection, a plurality of pieces of inspection request information (order information) may be provided for one and the same patient. For this reason, there is a possibility that wrong inspection result information may be linked with order information.

For example, assume that a formal order for upper inspection and a formal order for lower inspection are issued from a hospital information system. In this case, a doctor may then perform lower inspection in accordance with the formal order for upper inspection and record inspection result information of the lower inspection in link with the formal order for upper inspection.

Patent Document 1 (JP-A-2004-348687) discloses a system in which a link destination of inspection result information which has been linked with an intrasectoral order can be changed from the intrasectoral order to a formal order, or a formal order can be newly linked with inspection result information having no order. Even in this system, however, there is still a possibility that a wrong link may be established after the formal order is issued. The system disclosed in Patent Document 1 is described on the assumption that a formal order will be issued later, and therefore gives no consideration about how to deal with the case where a wrong link is established after a formal order is issued.

SUMMARY

An illustrative aspect of the invention is to provide an endoscopic inspection information administering system, an endoscopic inspection information administrating method, and a computer readable medium in which even when wrong inspection request information is linked with inspection result information, the link can be changed correctly.

[1] According to an aspect of the invention, an endoscopic inspection information administering system for administering inspection request information of endoscopic inspection issued outside an endoscopic sector and inspection result information of the inspection conducted in accordance with the inspection request information, while establishing a link between the inspection request information and the inspection result information, the system includes: a database in which the inspection request information and the inspection result information of the inspection conducted in accordance with the inspection request information are registered in link with each other; an unlinking unit which cancels a link between a first piece of the inspection request information selected from the inspection request information and a piece of the inspection result information linked with the first piece of the inspection request information, in accordance with an instruction issued through an input unit to unlink the first piece of the inspection request information; a retrieval display unit which retrieves, from the database, pieces of the inspection request information including the same patient-specific information as patient-specific information included in a second piece of the inspection request information selected from the inspection request information, in accordance with an instruction issued through the input unit to link the second piece of the inspection request information, and displays the retrieved pieces of the inspection request information on a display unit; and a recording control unit which records, into the database, a piece of the inspection request information selected from the pieces of the inspection request information displayed by the retrieval display unit and a piece of the inspection result information (i) which includes the same patient-specific information as the patient-specific information of the second piece of the inspection request information and (ii) which has not been linked with any piece of the inspection request information, while establishing a link between the selected piece of the inspection request information and the piece of the inspection result information.

[2] According to another aspect of the invention, an endoscopic inspection information administering method for administering inspection request information of endoscopic inspection issued outside an endoscopic sector and inspection result information of the inspection conducted in accordance with the inspection request information, while establishing a link between the inspection request information and the inspection result information, the method includes: canceling a link between a first piece of the inspection request information selected from the inspection request information in a database in which the inspection request information and the inspection result information of the inspection conducted in accordance with the inspection request information are registered in link with each other, and a piece of the inspection result information linked with the first piece of the inspection request information, in accordance with an instruction issued through an input unit to unlink the first piece of the inspection request information; retrieving, from the database, pieces of the inspection request information including the same patient-specific information as patient-specific information included in a second piece of the inspection request information selected from the inspection request information, in accordance with an instruction issued through an input unit to link the second piece of the inspection request information, and displaying the retrieved pieces of the inspection request information on a display unit; and recording, into the database, a piece of the inspection request information selected from the displayed pieces of the inspection request information displayed and a piece of the inspection result information which includes the same patient-specific information as the patient-specific information of the second piece of the inspection request information and which has not been linked with any piece of the inspection request information, while establishing a link between the selected piece of the inspection request information and the piece of the inspection result information.

[3] According to another aspect of the invention, a computer readable medium stores a program causing a computer to execute the endoscopic inspection information administrating method of [2].

With the configuration of any one of [1] to [3], even when wrong inspection request information is linked with inspection result information, the link can be changed correctly.

DETAILED DESCRIPTION

An exemplary embodiment of the invention will be described below with reference to the drawings.

Figure 1:
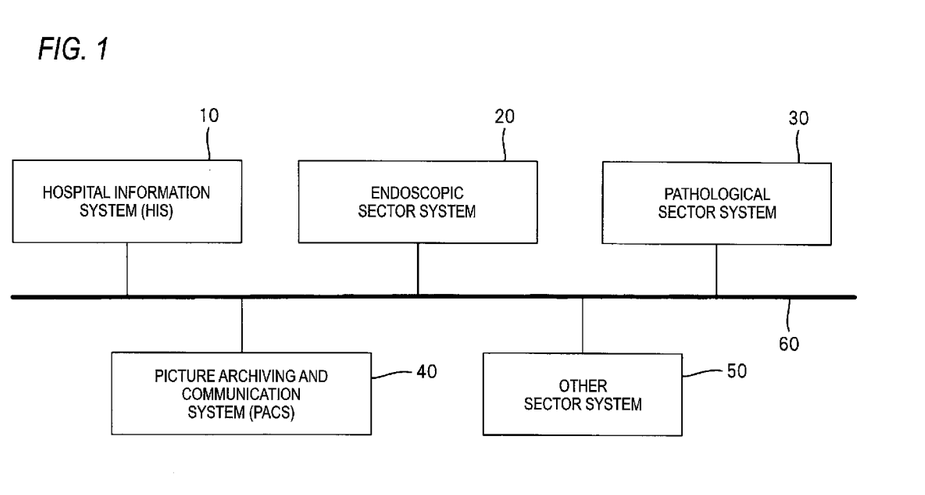
FIG. 1 is a diagram showing an overall configuration of a hospital system.

FIG. 1 is a diagram showing an overall configuration of a hospital system. The system shown in FIG. 1 includes a hospital information system (HIS) 10, an endoscopic sector system 20, a pathological sector system 30, a picture archiving and communication system (PACS) 40, and an other sector system 50. These systems 10 to 50 are connected to a hospital LAN 60 so that these systems 10 to 50 can work with one another.

The HIS 10 is a comprehensive system including a medical coding/billing system, a medical practice reservation system, a medical practice information system, etc. The HIS 10 has an electronic medical record database etc. Electronic medical records in which medical practice information of patients has been recorded are stored in the electronic medical record database.

Assume that an inspection request from another medical department is sent to the endoscopic sector. When information about the inspection request (order) (hereinafter referred to as inspective request information) in this case is issued, the inspection request information is transmitted to the endoscopic sector system 20 through the HIS 10.

For example, the inspection request information includes patient's information, order key information ("order number", "date and time of occurrence", etc.), request source information ("requesting department name", "requesting doctor name", "request date", etc.), order information ("requested disease name", "inspection purpose", "inspection kind", "inspection item", "inspection region", "comment", etc.), inspection reservation information ("inspection date", "conduct time", etc.), etc. The patient's information is information about a patient, including "patient ID as patient-specific information", "patient name", "birth date", "age", "sex", "inpatient/outpatient distinction", etc.

The endoscopic sector system 20 is a system for administering an endoscopic sector.

The pathological sector system 30 is a system for administering a pathological sector.

The PACS 40 is a system for electronically storing, retrieving and analyzing each inspection image from a medical image diagnostic device such as an endoscopic inspection device, a CT or an MRI.

The other sector system 50 is a system for administering the other sectors.

Figure 2:
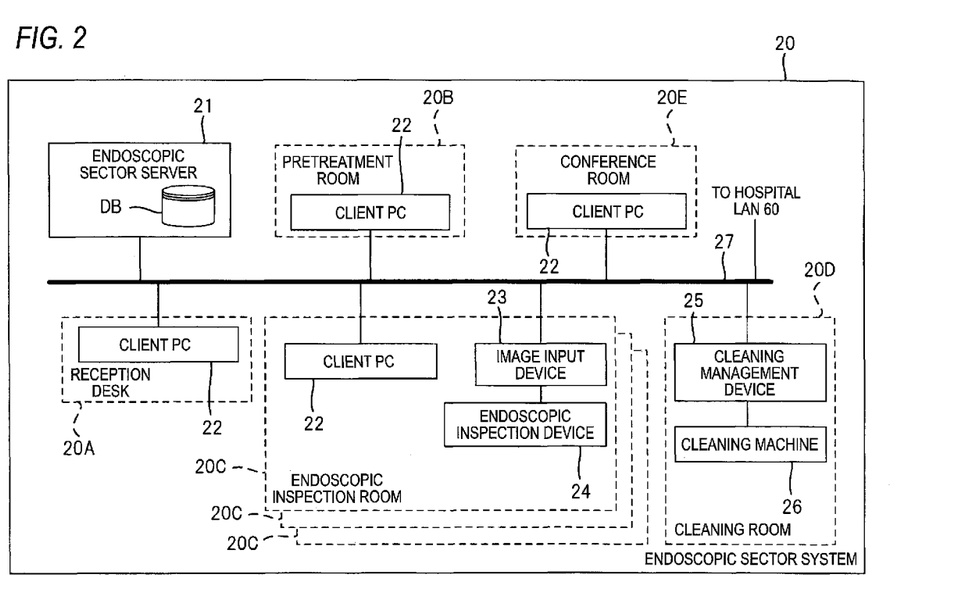
FIG. 2 is a diagram showing a schematic configuration of an endoscopic sector system in the system shown in FIG. 1.

FIG. 2 is a diagram showing a schematic configuration of an endoscopic sector system in the system shown in FIG. 1. The endoscopic sector includes a reception desk 20A, a pretreatment room 20B, a plurality of endoscopic inspection rooms (hereinafter referred to as inspection rooms" simply) 20C, a cleaning room 20D, and a conference room 20E.

The reception desk 20A is a site for accepting inspections. The pretreatment room 20B is a room for interview and pretreatment before each endoscopic inspection. The inspection rooms 20C are rooms for endoscopic inspections. The cleaning room 20D is a room for cleaning endoscopes etc. used for the endoscopic inspections.

The endoscopic sector system 20 shown in FIG. 2 has an endoscopic sector server 21, client PCs 22, image input devices 23, endoscopic inspection devices 24, a cleaning management device 25 and a cleaning machine 26. The endoscopic sector server 21, the client PCs 22, the image input devices 23 and the cleaning management device 25 are connected to an intrasectoral LAN 27. The intrasectoral LAN 27 is connected to the hospital LAN 60.

Figure 3:
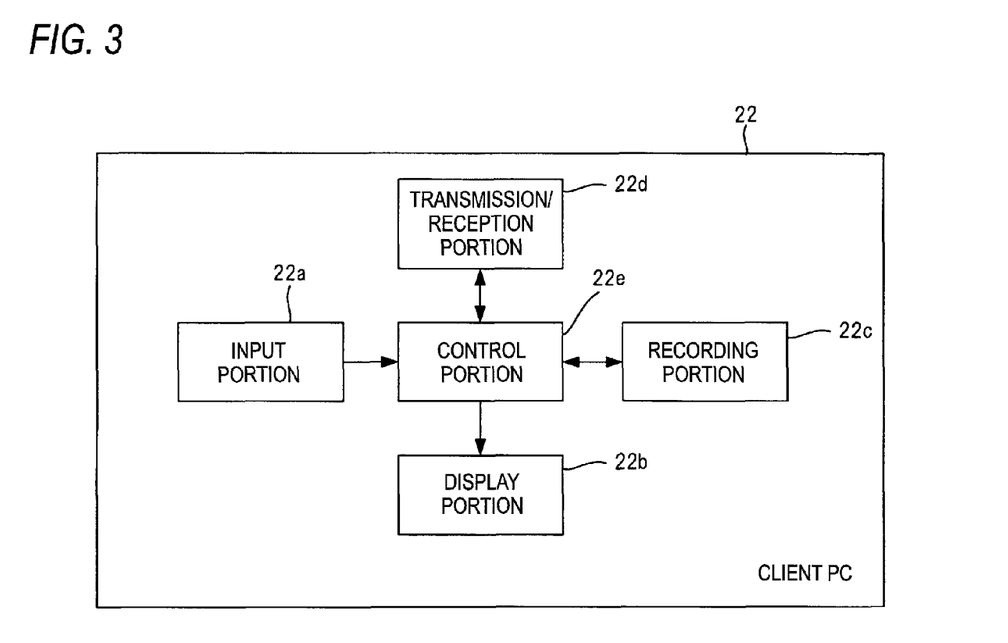
FIG. 3 is a diagram showing a schematic configuration of each client PC shown in FIG. 2.

FIG. 3 is a block diagram showing an internal configuration of each client PC in the endoscopic sector system shown in FIG. 2. As shown in FIG. 3, each client PC 22 is constituted by an input portion 22a, a display portion 22b, a recording portion 22c, a transmission/reception portion 22d and a control portion 22e.

The input portion 22a is an input unit for performing various inputs. The input portion 22a is constituted by input devices such as a keyboard and a touch panel, and pointing devices such as a mouse and a trackball.

The display portion 22b is a display unit for performing various displays such as an image and a report. The display portion 22b is constituted by an LCD, a CRT or the like.

The recording portion 22c is constituted by a hard disk or the like for recording various data.

The transmission/reception portion 22d is constituted by a transmission/reception interface circuit or the like. The transmission/reception portion 22d executes processing for transmitting/receiving various instructions, various requests and various data through the intrasectoral LAN 27.

The control portion 22e includes a processor such as a CPU (Central Processing Unit), a program storage portion such as an ROM (Read-Only Memory) for storing programs, and a storage portion. The storage portion is constituted by a system memory, a nonvolatile RAM (Random Access Memory), or the like, which forms work areas for executing the programs.

The control portion 22e controls the respective portions of the client PC 22 in accordance with the programs, various requests transmitted from the outside through the intrasectoral LAN 27, instruction information inputted from the input portion 22a, etc.

The image input devices 23 and the endoscopic inspection devices 24 are placed in the inspection rooms 20C respectively.

Each image input device 23 is connected to the endoscopic inspection device 24 in the inspection room 20C where the image input device 23 is placed. The image input device 23 is a device by which image data obtained by capturing images with the endoscopic inspection device 24 connected thereto is supplied to the endoscopic sector server 21. The image data supplied by the image input device 23 is stored by the PACS 40 under the control of the endoscopic sector server 21. Alternatively, an endoscopic inspection device integrated with the image input device 23 may be used as the endoscopic inspection device 24.

The cleaning machine 26 and the cleaning management device 25 are placed in the cleaning room 20D. The cleaning machine 26 is a device for cleaning endoscopes etc. used for endoscopic inspections.

The cleaning management device 25 is a computer which is connected to the cleaning machine 26 and by which information of a cleaning history or the like of the cleaning machine 26 is registered in the endoscopic sector server 21.

The endoscopic sector server 21 is a computer for generally controlling the client PCs 22, the image input devices 23 and the cleaning management device 25. A database DB is built in the endoscopic sector server 21. Various kinds of information (inspection request information, inspection result information, etc.) are stored in the database DB.

A predetermined application program is installed in each client PC 22. By the program, the client PC 22 can refer to and edit data recorded in the database DB and register data in the database DB.

Figure 4:
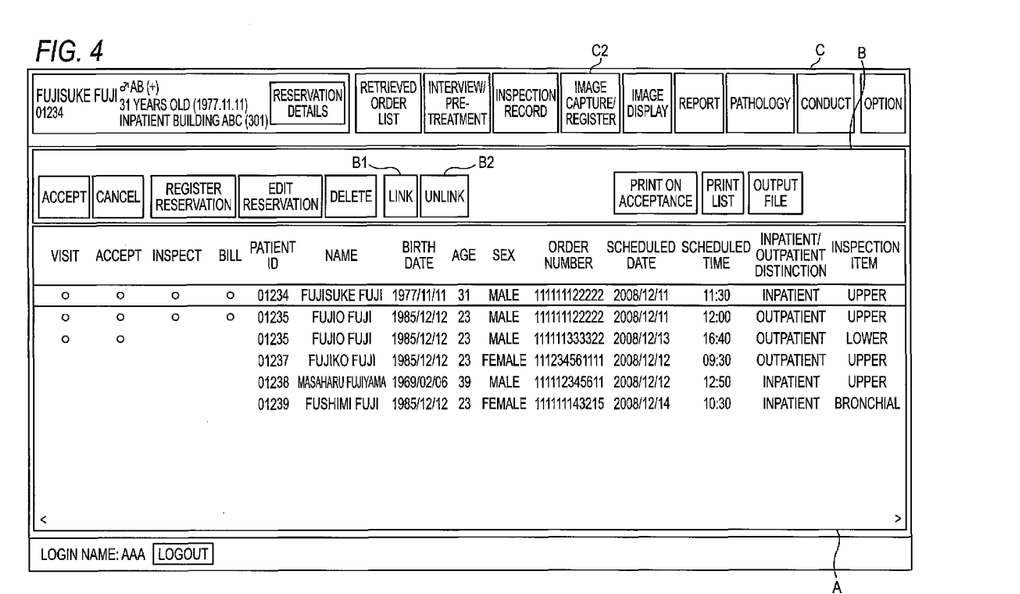
FIG. 4 is a view showing a basic screen of an application installed in the client PC shown in FIG. 2.

For example, a basic screen of this application is shown in FIG. 4. When a user starts up the application in the client PC 22 and logs into the application, the control portion 22e acquires basic screen data from the database DB and makes the display portion 22b display the basic screen shown in FIG. 4.

The basic screen is constituted by a region A for displaying a list of inspection request information (partially extracted information), a region B for displaying various operation buttons, and a region C for displaying launchers available for the inspection request information selected on the list.

Processing items including "visit", "accept", "inspect", "bill", etc. are provided for each piece of inspection request information in the list of the region A. When the processing indicated by each processing item is completed for each piece of inspection request information, the mark "○" is displayed for the processing item.

Data for displaying the mark is registered in the database DB by the endoscopic sector server 21 as soon as each processing is completed. When, for example, inspection is completed based on inspection request information, the endoscopic sector server 21 registers information, which indicates the completion of the inspection, into the database DB in association with the inspection request information. In this manner, the mark "○" is displayed in the processing item "inspect". The information indicating whether each processing has been completed or not may be inputted manually, or may be automatically notified by the client PC 22 or the endoscopic inspection device 24.

A specific example of a work procedure to be performed by a doctor will be described below.

When inspection request information is transmitted from the HIS 10, the inspection request information is registered in the database DB by the endoscopic sector server 21. A part of the registered inspection request information is displayed in the region A shown in FIG. 4. FIG. 4 shows an example in which two pieces of inspection request information are issued. One of the two pieces is inspection request information for a request to perform upper endoscopic inspection on a patient whose patient ID is 01235 (hereinafter referred to as upper inspection request information), and the other is inspection request information for a request to perform lower endoscopic inspection on the same patient (hereinafter referred to as lower inspection request information).

The doctor in an inspection room 20C clicks and selects, from pieces of inspection request information shown in FIG. 4, upper inspection request information including the patient ID (01235) of the patient visiting the inspection room. The doctor then clicks an "image capture/register" button C2 in the region C.

The image capture/register button C2 is a button for displaying an operation screen on which inspection based on the inspection request information selected in the region A can be carried out by use of the endoscopic inspection device 24 and captured image data or the like obtained by the inspection can be registered.

In accordance with the operation screen displayed by clicking the image capture/register button C2, the doctor carries out endoscopic inspection on the patient whose patient ID is 01235. The control portion 22e of the client PC 22 in the inspection room 20C can communicate with the endoscopic inspection device 24 in the same inspection room 20C. When an inspection start button displayed on the operation screen is clicked, the control portion 22e of the client PC 22 transmits an inspection start signal to the endoscopic inspection device 24.

The endoscopic inspection device 24 uses the inspection start signal as a trigger to start capturing moving images. A moving image which is being captured is displayed on the operation screen in real time. When an image capture button displayed on the operation screen is clicked, the control portion 22e of the client PC 22 transmits an image capturing signal to the endoscopic inspection device 24.

The endoscopic inspection device 24 uses the image capturing signal as a trigger to capture a still picture. Image data of the captured still image is displayed on the operation screen in real time, and stored by the PACS 40.

When an inspection end button displayed on the operation screen is clicked, the control portion 22e of the client PC 22 transmits an inspection end signal to the endoscopic inspection device 24. The endoscopic inspection device 24 uses the inspection end signal as a trigger to end the image capturing.

When the inspection end button is clicked, the control portion 22e of the client PC 22 registers inspection result information into the database DB so as to link the inspection result information with the inspection request information (upper inspection request information of the patient ID 01235) selected in the region A. The inspection result information includes link information indicating the place where the captured image data obtained by the inspection has been stored, and information about the contents of the conducted inspection (patient ID of inspected patient, inspection item, inspection date and time, etc.). When these pieces of information are registered in the database DB, the mark "○" is displayed in the item "inspect" corresponding to the upper inspection request information on the screen shown in FIG. 4.

Of the inspection result information, the information about the contents of the conducted inspection can be generated manually with reference to information inputted into the endoscopic inspection device 24. The inspection date and time may be generated by detection of the date and time when the inspection start button was clicked. As a method for recording the two pieces of data in link with each other, for example, a method of recording the two pieces of data with a shared identification number added to the tails of file names of the two pieces of data may be used.

The method for recording the inspection request information and the inspection result information in link with each other is not limited to the aforementioned method. For example, the endoscopic inspection device 24 conducts inspection independently without using the image capture/register button C2, and the image input device 23 then records inspection result information of the inspection into the database DB. After that, the control portion 22e of the client PC 22 allows a user to select a piece of inspection request information to be linked with the inspection result information, from a list displayed in the region A shown in FIG. 4. The control portion 22e of the client PC 22 records the selected piece of inspection request information into the database DB so as to link the piece of inspection request information with the inspection result information.

When a magnetic card reader mounted on the endoscopic inspection device 24 reads a patient ID card possessed by a patient, patient ID, inspection item, inspection date and time, etc. of the inspection result information can be inputted to the image input device 23.

Here, description will be made in the case where the doctor links inspection result information of lower endoscopic inspection (hereinafter referred to as lower inspection result information simply) with upper inspection request information by accident by way of example.

In such a case, after the completion of the inspection, the doctor clicks and selects upper inspection request information of the patient ID 01235 on the screen shown in FIG. 4, and then clicks an unlink button B2 displayed in the region B. The unlink button B2 is a button for cancelling the link between the inspection request information selected in the region A and the inspection result information linked therewith (abandoning the link with each other).

When the unlink button B2 is clicked, the control portion 22e of the client PC 22 cancels the link between the selected upper inspection request information and the lower inspection result information linked therewith. For example, as described above, the cancel of the link is achieved by deleting identification numbers added to the tails of file names of the upper inspection request information and the lower inspection result information.

Next, the doctor clicks and selects lower inspection request information of the patient ID 01235 on the screen shown in FIG. 4, and then clicks a link button B1 displayed in the region B. The link button B1 is a button by which inspection request information selected in the region A can be linked with inspection result information (which has not been linked) including the same patient ID as that of the inspection request information.

When the link button B1 is clicked, the control portion 22e of the client PC 22 retrieves, from the database DB, inspection request information including the same patient ID as the patient ID included in the lower inspection request information which is currently selected. The control portion 22e of the client PC 22 makes the display portion 22b display the retrieved inspection request information as a list of to-be-linked candidates. In addition, of inspection result information including the same patient ID as that of the lower inspection request information which is currently selected, information which has not been linked with any inspection request information is displayed on the display portion 22b.

Figure 5:
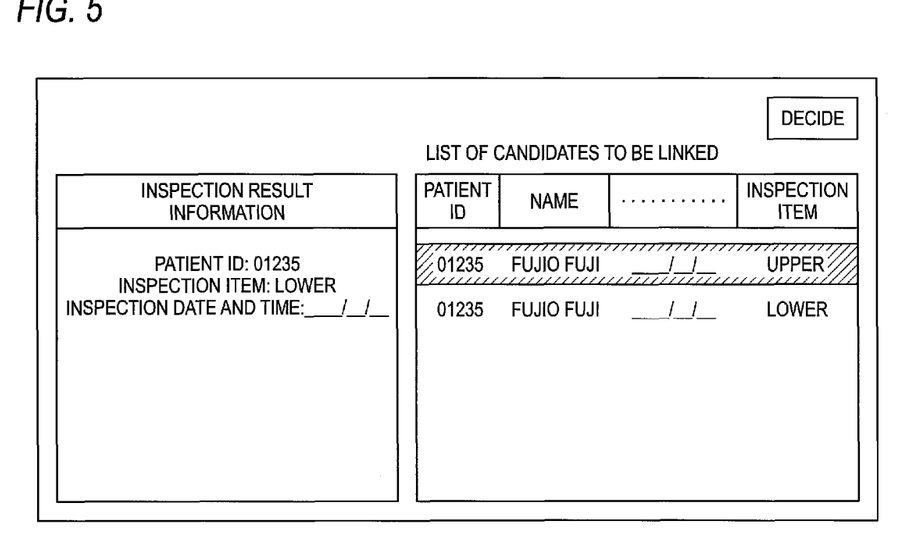
FIG. 5 is a view showing an example of a screen to which the basic screen shown in FIG. 4 is switched when a link button is pushed on the basic screen.

FIG. 5 is a view showing an example of a screen displaying inspection result information and a list of candidates with which the inspection result information may be linked. As shown in FIG. 5, lower inspection result information which includes the same patient ID as that of the lower inspection request information selected on the screen shown in FIG. 4 and which has not been linked with any inspection request information is displayed in a left portion of the screen. In addition, a list of to-be-linked candidates is displayed in a right portion of the screen.

When the screen shown in FIG. 5 is displayed, the doctor clicks and selects, from the list of to-be-linked candidates, inspection request information (which is lower inspection request information in this case) which the doctor wants to link with the lower inspection result information displayed in the left portion of the screen. The doctor then clicks a decide button.

The control portion 22e of the client PC 22 records, into the database DB, the inspection request information (lower inspection request information) selected by the doctor and the inspection result information (lower inspection result information) displayed in the left portion of the screen, so as to link the two with each other.

By the aforementioned operation, the lower inspection result information can be released from being linked with the upper inspection request information, and can be recorded in link with the lower inspection request information which is the correct inspection request information for the lower inspection result information.

Next, description will be made on modifications of the endoscopic sector system in the system shown in FIG. 1.

(First Modification)

When a list of to-be-linked candidates is displayed in accordance with clicking of the link button B1, the control portion 22e of the client PC 22 in the endoscopic sector system according to this modification performs control so that only one piece of inspection request information which includes the same patient ID as that of inspection request information currently selected and which includes the same information as the information of the inspection item included in inspection result information which has not been linked (information displayed in the left portion of the screen shown in FIG. 5) is displayed as the to-be-linked candidate. In the example of the screen shown in FIG. 5, only one piece of inspection request information including "lower" as the inspection item is displayed in the right portion of the screen.

With this configuration, a correct piece of inspection request information with which inspection result information should be linked can be selected easily. In addition, it is possible to prevent such a situation that upper inspection request information may be linked with lower inspection result information by accident.

(Second Modification)

When a list of to-be-linked candidates is displayed in accordance with clicking of the link button B1, the control portion 22e of the client PC 22 in the endoscopic sector system according to this modification performs control so that one piece of inspection request information which includes the same patient ID as that of inspection request information currently selected and which includes the same information as the information of the inspection item included in inspection result information which has not been linked (information displayed in the left portion of the screen shown in FIG. 5) is displayed in distinction from the other pieces of inspection request information.

When, for example, information of the inspection item included in the inspection result information is "lower" as shown in FIG. 5, lower inspection request information including "lower" as the inspection item, of the inspection request information displayed in the list of to-be-linked candidates is highlighted. With this configuration, a correct piece of inspection request information with which inspection result information should be linked can be selected easily.

(Third Modification)

In the endoscopic sector system according to this modification, the control portion 22e of the client PC 22 periodically refers to inspection request information and inspection result information registered in the database DB, and automatically determines whether a link therebetween is correct or not. For example, the control portion 22e of the client PC 22 checks whether inspection items of the two pieces of information coincide with each other or not. When it is concluded that the inspection items do not coincide with each other because of a wrong link, the wrong link may be displayed in an inspection request information list (in the region A of FIG. 4) in a recognizable way. In this manner, the user can be urged to rearrange the link, so that the user-friendliness can be improved.

As described above, the following matters are disclosed in the specification.

There is disclosed that an endoscopic inspection information administering system for administering inspection request information of endoscopic inspection issued outside an endoscopic sector and inspection result information of the inspection conducted in accordance with the inspection request information, while establishing a link between the inspection request information and the inspection result information, the system includes: a database in which the inspection request information and the inspection result information of the inspection conducted in accordance with the inspection request information are registered in link with each other; an unlinking unit which cancels a link between a first piece of the inspection request information selected from the inspection request information and a piece of the inspection result information linked with the first piece of the inspection request information, in accordance with an instruction issued through an input unit to unlink the first piece of the inspection request information; a retrieval display unit which retrieves, from the database, pieces of the inspection request information including the same patient-specific information as patient-specific information included in a second piece of the inspection request information selected from the inspection request information, in accordance with an instruction issued through the input unit to link the second piece of the inspection request information, and displays the retrieved pieces of the inspection request information on a display unit; and a recording control unit which records, into the database, a piece of the inspection request information selected from the pieces of the inspection request information displayed by the retrieval display unit and a piece of the inspection result information (i) which includes the same patient-specific information as the patient-specific information of the second piece of the inspection request information and (ii) which has not been linked with any piece of the inspection request information, while establishing a link between the selected piece of the inspection request information and the piece of the inspection result information.

With this configuration, when a wrong piece of inspection request information is linked with a piece of inspection result information, the link can be changed correctly.

In the disclosed endoscopic inspection information administering system, the retrieval display unit may selectively display, of the pieces of the inspection request information which include the same patient-specific information as the patient-specific information included in the second piece of the inspection request information, one piece including the same information as information of an inspection item included in a piece of the inspection result information (i) which includes the same patient-specific information as the patient-specific information of the second piece of the inspection request information and (ii) which has not been linked to any piece of the inspection request information.

With this configuration, one piece of inspection request information which includes the same inspection item as the inspection item included in a piece of inspection result information which has not yet been linked is displayed as the to-be-linked candidate. It is therefore possible to arrange a correct link easily.

In the disclosed endoscopic inspection information administering system, the retrieval display unit may display, of the pieces of the inspection request information which include the same patient-specific information as the patient-specific information included in the second piece of the inspection request information, one piece including the same information as information of an inspection item included in a piece of the inspection result information (i) which includes the same patient-specific information as the patient-specific information of the second piece of the inspection request information and (ii) which has not been linked to any piece of the inspection request information, in distinction from the other pieces of the inspection request information.

With this configuration, one piece of inspection request information which includes the same inspection item as the inspection item included in a piece of inspection result information which has not yet been linked is displayed in distinction from the other pieces of inspection request information. It is therefore possible to easily search for a correct piece of inspection request information to be linked.

In the endoscopic inspection information administering system as described above, the retrieval display unit may display, on one and the same screen, the retrieved pieces of the inspection request information and the piece of the inspection result information (i) which includes the same patient-specific information as the patient-specific information of the second piece of the inspection request information and (ii) which has not been linked with any piece of the inspection request information.

With this configuration, a correct link can be arranged while referring to both inspection result information and inspection request information.

Further, there is disclosed an endoscopic inspection information administering method for administering inspection request information of endoscopic inspection issued outside an endoscopic sector and inspection result information of the inspection conducted in accordance with the inspection request information, while establishing a link between the inspection request information and the inspection result information, the method comprising: canceling a link between a first piece of the inspection request information selected from the inspection request information in a database in which the inspection request information and the inspection result information of the inspection conducted in accordance with the inspection request information are registered in link with each other, and a piece of the inspection result information linked with the first piece of the inspection request information, in accordance with an instruction issued through an input unit to unlink the first piece of the inspection request information; retrieving, from the database, pieces of the inspection request information including the same patient-specific information as patient-specific information included in a second piece of the inspection request information selected from the inspection request information, in accordance with an instruction issued through an input unit to link the second piece of the inspection request information, and displaying the retrieved pieces of the inspection request information on a display unit; and recording, into the database, a piece of the inspection request information selected from the displayed pieces of the inspection request information displayed and a piece of the inspection result information which includes the same patient-specific information as the patient-specific information of the second piece of the inspection request information and which has not been linked with any piece of the inspection request information, while establishing a link between the selected piece of the inspection request information and the piece of the inspection result information.

In the disclosed endoscopic inspection information administering method, the displaying may include selectively displaying, of the pieces of the inspection request information which include the same patient-specific information as the patient-specific information included in the second piece of the inspection request information, one piece including the same information as information of an inspection item included in a piece of the inspection result information (i) which includes the same patient-specific information as the patient-specific information of the second piece of the inspection request information and (ii) which has not been linked to any piece of the inspection request information.

In the disclosed endoscopic inspection information administering method, the displaying may include displaying, of the pieces of the inspection request information which include the same patient-specific information as the patient-specific information included in the second piece of the inspection request information, one piece including the same information as information of an inspection item included in a piece of the inspection result information (i) which includes the same patient-specific information as the patient-specific information of the second piece of the inspection request information and (ii) which has not been linked to any piece of the inspection request information, in distinction from the other pieces of the inspection request information.

In the endoscopic inspection information administering method, the displaying may include displaying, on one and the same screen, the retrieved pieces of the inspection request information and the piece of the inspection result information (i) which includes the same patient-specific information as the patient-specific information of the second piece of the inspection request information and (ii) which has not been linked with any piece of the inspection request information.

Further, there is disclosed a computer readable medium storing a program causing a computer to execute the endoscopic inspection information administrating method described above.

What is claimed is:

1. An endoscopic inspection information administering system, the system comprising:
    a server receiving, from outside of an endoscopic sector, inspection request information which requests an endoscopic inspection and which comprises a patient identification, an identification of a body part and storing in a database the received inspection request information, receiving inspection result information from the endoscopic inspection conducted based on the stored inspection request information and storing the received inspection result information, and registering by linking to each other the stored inspection request information and the inspection result information;
    a client having a display unit, the client comprising:
    an unlinking unit which cancels a link between a first piece of the inspection request information selected from the inspection request information and a piece of the inspection result information incorrectly linked with the first piece of the inspection request information, in accordance with an instruction issued through an input unit to unlink the first piece of the inspection request information, wherein the first piece of the inspection request information is incorrectly linked with the first piece of the inspection result information in that: the patient identification of the first piece of the inspection request information matches the patient identification of the first piece of the inspection result information, and the identification of the body part of the first piece of the inspection request information does not match the body part identified in the first piece of the inspection result information;
    a retrieval display unit which retrieves, from the database, a second piece of the inspection request information different from the first piece of the inspection request information, and displays the second piece of the inspection request information on the display unit wherein the patient identification of the second piece of the inspection request information matches the patient identification of the first piece of the inspection result information; and
    a registering control unit which registers the displayed second piece of inspection request information and the first piece of the inspection result information by establishing a correct link between the displayed second piece of inspection request information and the first piece of the inspection result information, wherein the correct link is such that, the second piece of the inspection request information has not been linked with any piece of the inspection result information, the patient identification and the identification of the body part in the second piece of the inspection request information matches the patient identification and the body part identified in the first inspection result information,
    wherein the register control unit stores the second piece of the inspection request information linked with the first inspection result information, and
    wherein at least one of the unlinking unit, the retrieval display unit and the recording control unit is executed by a processor.

2. The endoscopic inspection information administering system according to claim 1, wherein:
    the retrieval display unit selectively displays, of pieces of the inspection request information which include the same patient identification information as the patient-identification information included in the second piece of the inspection request information, one piece including the same information as information of an inspection item included in a piece of the inspection result information (i) which includes the same patient identification information as the patient identification information of the second piece of the inspection request information and (ii) which has not been linked to any piece of the inspection request information.

3. The endoscopic inspection information administering system according to claim 1, wherein:
    the retrieval display unit displays, of pieces of the inspection request information which include the same patient identification information as the patient identification information included in the second piece of the inspection request information, one piece including the same information as information of an inspection item included in a piece of the inspection result information (i) which includes the same patient identification information as the patient identification information of the second piece of the inspection request information and (ii) which has not been linked to any piece of the inspection request information, in distinction from the other pieces of the inspection request information.

4. The endoscopic inspection information administering system according to claim 1, wherein:
    the retrieval display unit displays, on one and the same screen, retrieved pieces of the inspection request information and the piece of the inspection result information (i) which includes the same patient identification information as the patient identification-information of the second piece of the inspection request information and (ii) which has not been linked with any piece of the inspection request information.

5. A non-transitory computer readable medium storing a program causing a computer to execute an endoscopic inspection information administrating method between a server and a client, the method comprising:

receiving, from outside of an endoscopic sector inspection request information which requests an endoscopic inspection and which comprises a patient identification, an identification of a body part;

storing in a database the received inspection request information;

receiving inspection result information from the endoscopic inspection conducted based on the stored inspection request information;

storing in the database the received inspection result information;

registering by linking to each other the stored inspection request information and the inspection result information;

canceling a link between a first piece of the inspection request information selected from the inspection request information and a first piece of the inspection result information incorrectly linked with the first piece of the inspection request information, in accordance with an instruction issued through an input unit to unlink the first piece of the inspection request information, wherein the first piece of the inspection request information is incorrectly linked with the first piece of the inspection result information in that: the patient identification of the first piece of the inspection request information matches the patient identification of the first piece of the inspection result information, and the identification of the body part of the first piece of the inspection request information does not match the body part identified in the first piece of the inspection result information;

retrieving, from the database, a second piece of the inspection request information different from the first piece of the inspection request information, displaying the second piece of the inspection request information on a display unit wherein the patient identification of the second piece of the inspection request information matches the patient identification of the first piece of the inspection result information; and registering the displayed second piece of inspection request information and the first piece of the inspection result information by establishing a correct link between the displayed second piece of inspection request information the first piece of the inspection result information, wherein the correct link is such that the second piece of the inspection request information has not been linked with any piece of the inspection result information, the patient identification and the identification of the body part in the second piece of the inspection request information matches the patient identification and the body part identified in the first inspection result information; and storing the second piece of the inspection request information linked with the first inspection result information.

6. The endoscopic inspection information administering system according to claim 5, wherein:

the retrieval display unit selectively displays, of pieces of the inspection request information which include the same patient identification information as the patient identification information included in the second piece of the inspection request information, one piece including the same information as information of an inspection item included in a piece of the inspection result information (i) which includes the same patient identification information as the patient identification information of the second piece of the inspection request information and (ii) which has not been linked to any piece of the inspection request information.

7. The endoscopic inspection information administering system according to claim 5, wherein:

the retrieval display unit displays, of pieces of the inspection request information which include the same patient identification information as the patient identification information included in the second piece of the inspection request information, one piece including the same information as information of an inspection item included in a piece of the inspection result information (i) which includes the same patient identification information as the patient identification information of the second piece of the inspection request information and (ii) which has not been linked to any piece of the inspection request information, in distinction from the other pieces of the inspection request information.

8. The endoscopic inspection information administering system according to claim 5, wherein:

the retrieval display unit displays, on one and the same screen, retrieved pieces of the inspection request information and the piece of the inspection result information (i) which includes the same patient identification information as the patient identification information of the second piece of the inspection request information and (ii) which has not been linked with any piece of the inspection request information.

* * * * *